US00PP18439P2

(12) United States Plant Patent

Hardison et al.

(10) Patent No.: US PP18,439 P2
(45) Date of Patent: Jan. 15, 2008

(54) HYBRID VARIETY OF (TEXAS BLUEGRASS×KENTUCKY BLUEGRASS)× KENTUCKY BLUEGRASS DESIGNATED 'HB 329'

(50) Latin Name: (Texas Bluegrass×Kentucky Bluegrass)×Kentucky Bluegrass hybrid
Varietal Denomination: HB 329

(75) Inventors: John R. Hardison, Corvallis, OR (US); Jay B. Burr, Salem, OR (US); James R. Frelich, Salem, OR (US); George Marquez, Albany, OR (US)

(73) Assignee: OMS Investments, Inc., Los Angeles, CA (US)

( * ) Notice: Subject to any disclaimer, the term of this patent is extended or adjusted under 35 U.S.C. 154(b) by 151 days.

(21) Appl. No.: 11/208,473
(22) Filed: Aug. 19, 2005
(51) Int. Cl.
*A01H 5/00* (2006.01)

(52) U.S. Cl. ..... Plt./393
(58) Field of Classification Search ..... Plt./393

See application file for complete search history.

(56) References Cited

U.S. PATENT DOCUMENTS

| | | | |
|---|---|---|---|
| PP3,150 | P | 5/1972 | Pepin et al. |
| PP3,156 | P | 5/1972 | Fuchigami et al. |
| PP3,186 | P | 5/1972 | Barenbrug et al. |
| PP4,336 | P | 11/1978 | Mayer et al. |
| PP6,280 | P | 9/1988 | Meier et al. |
| PP6,537 | P | 1/1989 | Meier et al. |
| PP6,538 | P | 1/1989 | Meier et al. |
| PP6,585 | P | 2/1989 | Meier et al. |
| PP7,831 | P | 3/1992 | Meier et al. |
| PP8,490 | P | 12/1993 | Meier et al. |
| PP9,036 | P | 1/1995 | Meier et al. |
| PP9,209 | P | 7/1995 | Meier et al. |
| PP9,611 | P | 7/1996 | Meier |
| PP9,848 | P | 4/1997 | Meier et al. |
| PP9,977 | P | 7/1997 | Meier et al. |
| PP10,080 | P | 10/1997 | Meier et al. |
| PP10,081 | P | 10/1997 | Meier et al. |
| PP10,384 | P | 5/1998 | Meier et al. |
| PP10,925 | P | 5/1999 | Meier et al. |
| PP11,520 | P | 9/2000 | Meier et al. |
| PP11,536 | P | 10/2000 | Meier et al. |
| PP12,435 | P2 | 3/2002 | Meier et al. |

OTHER PUBLICATIONS

Drought resistance of two texas Bluegrass hybrids compared with kentucky Bluegrass and Tall Fescue. Bremer d. et al.K–State Turfgrass Research. Report of Progress 911. 2003. p.67–77.*
Agronomy J., 41(8):393–394; Aug. 1949.
Beard et al., Beard's Turfgrass Encyclopedia for Golf Course Grounds Lawns Sports Fields, definition of apomixis, p. 23; 2009.
Bulletin of the Agricultural Experiment Station of the University of Tennessee, The Grasses of Tennessee—Part I, V(2):29, 45, 60–63, 94–97; Apr. 1892.
Curley et al., RAPD–Based Genetic Relationships in Kentucky Bluegrass: Comparison of Cultivars, Interspecific Hybrids, and Plant Introductions, reproduced from Crop Sci. 44:1299–1306; 2004.
Lamson–Scribner, American Grasses—II (Illustrated), U.S. Dept. of Agriculture, Bulletin No. 17:246; 1899.
Manual for Testing Agricultural and Vegetable Seeds, Agriculture Handbook, No. 30:67–70, 224–227; 396–397, Plates VIII–X; 1952.
Piper, Blue Grasses, Meadow–Grasses and Redtop in Forage Plants and Their Culture, pp. 155–171; 1919.
Porceddu et al., Linkage mapping in apomictic and sexual Kentucky bluegrass (*Poa Pratensis* L.) genotypes using a two way pseudo–testcross strategy based on AFLP and SAMPL markers, Theor Appl Genet, Feb. 2002;104(2–3):273–280.
Read et al., Registration of 'Reveille' Hybrid Bluegrass, Crop Science, 39:590; Mar.–Apr. 1999.
Read et al., Texas Bluegrass (*Poa arachnifera* Torr.) in Turfgrass Biology, Genetics, and Breeding, Casler and Duncan, eds., pp. 61–66; 2003.
Silveus et al., Texas Grasses, Classification and description of Grass, Descriptive Systematic Agrostology, Introduction–Illustrations XV–XVII, pp. 33–48; 1933.
Yearbook of Agriculture, U.S. Dept. of Agriculture, 75th Congress, 1st Session, House Document No. 28:1056–1070; 1937.
Yearbook of the U.S. Dept. of Agriculture, pp. 139, 145–146, Plates IV–V; 1908.

* cited by examiner

*Primary Examiner*—Kent Bell
*Assistant Examiner*—Annette Para

(57) ABSTRACT

A hybrid variety of (Texas bluegrass×Kentucky bluegrass)× Kentucky bluegrass as described, characterized by a moderately rapid establishment; a light green, dense turf; a wide leaf blade; aggressive rhizome growth; a reduced level of cotton on the seed; and a low to medium-low seed yield potential.

3 Drawing Sheets

BACKGROUND OF THE INVENTION

Field of the Invention

The present invention relates to a new and distinct hybrid variety of (Texas Bluegrass×Kentucky Bluegrass)×Kentucky Bluegrass that has been designated as 'HB 329' bluegrass.

Description of Related Art

A Texas Bluegrass×Kentucky Bluegrass hybrid designated 'Reveille' has been disclosed in PVP Certificate No. 9800337. Another Texas Bluegrass×Kentucky Bluegrass hybrid designated 'HB 129' has been disclosed in pending U.S. patent application Ser. No. 11/197,945, filed Aug. 5, 2005, claiming the benefit of provisional application No. 60/599,446, filed Aug. 5, 2004.

SUMMARY OF THE VARIETY

'HB 329' bluegrass originated as the progeny formed by crossing an interspecific hybrid bluegrass (Texas Bluegrass× Kentucky Bluegrass) designated HB 47 (a female plant 7-23×cv. 'Geronimo' male plant) as the female parent crossed with cv. 'Ascot' Kentucky bluegrass (*Poa pratensis* L.) as the pollen parent. As a result of this breeding, a distinct hybrid variety was produced asexually propagated by rhizomes, tillers and disseminules displaying perfect flowers, apomixis and turfgrass performance characteristics in the $F_1$ generation.

Interspecific hybrid bluegrass female plant HB 47 is an unreleased plant selected and maintained in Gervais, Oreg. for its tiller density, turf quality and lack of male reproductive organs. 'Ascot' Kentucky bluegrass was bred by The Scotts Company, Marysville, Ohio, and has been disclosed under the designation BA 77-279 Kentucky Bluegrass in U.S. Plant Pat. No. 9,977 P, issued Jul. 22, 1997).

The highly apomictic seed of 'HB 329' bluegrass was produced first at Gervais, Oreg. This seed was used to plant turf performance evaluation trials and later, seed production fields. The seed of 'HB 329' has been found to be stable. Asexual production of 'HB 329' initially was performed at Gervais, Oreg. by propagules (tillers and rhizomes) and by disseminules (modified caryopses produced by apomixis), and has consistently produced progeny plants indistinguishable from the first generation asexual reproduction of the instant plant. The apomixis level of 'HB329' is approximately 94%. The apomixis level was determined by examining field planting of 'HB 329' in two years of rating for apomictic origin and from plants grown in a controlled environment chamber from disseminules harvested over four growing seasons from field grown plants in Gervais, Oreg.

'HB 329' has a number of highly desirable characteristics, including a dark green color, a moderate level of seedling vigor; high sod strength; and shows above average downy mildew and melting out disease tolerance when compared to other hybrid bluegrasses and Kentucky bluegrass varieties. 'HB 329' has an upright leafy turf type growth habit, and a dark green color that can be maintained throughout an entire growing season. 'HB 329' demonstrates very good fall color and very good winter color under mild winter conditions. 'HB 329' has shown good shade tolerance including downy mildew tolerance.

'HB 329' has a moderate amount of cotton (webbing) on the caryopsis. 'HB 329' has a low to medium-low seed yield potential in the Kentucky bluegrass seed production region of the northwestern United States and has shown the potential for economic seed production.

In comparison with the Reveille and 'HB 129' hybrids, 'HB 329' has demonstrated a germination and emergence rate slower than HB 129 but more rapid than Reveille in both fall and spring sowings. 'HB 329' has shown more seed cotton as compared 'HB129' and has less than 'Reveille'. It is believed that the presence of the cotton on the Reveille seed results in poor seed recovery of this hybrid and causes 'Reveille' to be available predominantly as a vegetatively reproduced product from rhizome and tiller materials.

Texas bluegrass is a vigorous sod-forming perennial native in the Southeastern and Southern Plains States. Plants grow up to 3 feet on strong soil, with numerous leaves 6 to 12 inches long and 0.25 inch wide. The grass grows throughout the winter producing abundant, nutritious pasture which is highly palatable. This is a valuable species where native, but seeding is difficult. The species is dioecious, with male and female parents. It produces only limited quantities of seed which is covered with woolly hairs that are difficult to remove. Consequently, establishment of stands for agricultural use is limited. Accordingly, Texas bluegrass exhibits similar problems to those encountered with Reveille that are overcome by the present 'HB 329' hybrid.

In comparison with a number of Kentucky bluegrass varieties and with hybrid bluegrass varieties such as HB 129 and Reveille, 'HB 329' has an average to above-average seed size with a lower number of seeds per pound. The width of vegetative leaves of unmowed mature plants of 'HB 329' are of medium to wide. 'HB 329' has a short to intermediate flag leaf length and with fewer hairs on the upper margin of the ligule than 'HB 129', fewer hairs on the collar margin and dorsal side of the leaf sheath than 'HB 129' and Kentucky bluegrasses. 'HB 329' is shorter than 'HB 129' and 'Reveille' hybrid bluegrasses and is similar in plant height to 'Ascot' Kentucky bluegrass. 'HB 329' has fewer florets per spikelet than HB 129 and is similar to 'Reveille' hybrid bluegrass. Anther color is 87% purple and 13% yellow distinguishing 'HB 329' from 'HB 129' which is 100% purple.

BRIEF DESCRIPTION OF THE DRAWING

FIG. 1 is an 'HB 329' panicle;

FIG. 2 is an 'HB 329' seed; and

FIG. 3 is an 'HB 329' plant shortly after completing anthesis.

DETAILED DESCRIPTION OF THE VARIETY

'HB 329' (Texas bluegrass×Kentucky bluegrass)× Kentucky bluegrass hybrid which may also be designated as (*Poa arachnifera* Torr.×*Poa pratensis* L.)×*Poa pratensis* L. hybrid is perennial with creeping rhizomes forming a moderately dense turf. When plants overwinter in the field and grow undisturbed by clipping, culms are semi-erect averaging 42.1 cm in length. The vegetative leaf averages 2.7 mm in width. The flag leaf averages 6.35 cm in length, 3.3 mm in width, has a sheath length of 12.35 cm. The flag leaf averages fewer hairs on the ligule than 'HB 129' hybrid bluegrass. The panicle averages 8.2 cm in length. The lowest whorl of the panicle averages 4.4 branches. 'HB329' has 4.6 florets per spikelet on the $1^{st}$ whorl and 5.0 florets per spikelet for the $3^{rd}$ whorl. The lower and upper glumes of the first whorl are 3.7 and 3.6 mm respectively and the lower and upper glumes of the third whorl are 3.6 and 3.7 mm respectively.

For the vegetative leaf, the number of hairs is average for the leaf sheath margin, below average for the dorsal side of the leaf blade, below average for the upper margin of the ligule, and below average for the collar margin compared to other varieties. 'HB 329' differs from the Kentucky bluegrass varieties in regard to such morphological characteristics as seed length and width, culm length, and hairs on the collar margins of the vegetative leaf, on the upper surface of the vegetative leaf, on the ligule of the flag leaf and anther color.

'HB 329' produces inflorescences relatively early compared with Kentucky bluegrasses, and reaches anthesis later than many other Kentucky bluegrass and hybrid bluegrass varieties.

Since environmental conditions such as soil and climate may influence morphological characteristics to some extent, comparisons of 'HB 329' were made with Kentucky bluegrass varieties and HB 129 hybrid bluegrass under like conditions and the comparisons are set forth in Tables 1–10, as follows.

TABLE 1

Comparison of heading data, seed yield, and plant height of 'HB 329' and various Kentucky bluegrass varieties and HB 129 hybrid bluegrass for years 1 & 2.

| | Heading Date | | Seed Yield | | Plant Height | |
|---|---|---|---|---|---|---|
| Variety | Year 1 (Julian) | Year 2 | Year 1 (g/10 ft row) | Year 2 | Year 1 (cm) | Year 2 |
| 'HB 329' | 108.2 | 100.8 | 11.2 | 7.4 | 51.1 | 54.3 |
| HB 129 | 114.4 | 108.6 | 47.3 | 27.1 | 64.2 | 65.4 |
| Midnight | 126.3 | 136.3 | 33.4 | 12.0 | 54.2 | 45.5 |
| America | 125.3 | 122.8 | 29.2 | 20.4 | 40.1 | 43.3 |
| Ram I | 120.0 | 120.9 | 22.5 | 25.5 | 47.2 | 48.8 |
| Julia | 111.8 | 118.3 | 36.6 | 20.8 | 63.6 | 60.8 |
| Baron | 118.1 | 116.0 | 58.4 | 36.9 | 51.8 | 52.7 |
| Adelphia | 126.3 | 115.9 | 10.2 | 17.9 | 53.8 | 59.2 |
| Nugget | 121.1 | 114.5 | 4.7 | 4.3 | 34.3 | 30.1 |
| Langara | 118.1 | 114.3 | 31.9 | 34.8 | 46.2 | 56.0 |
| Touchdown | 105.4 | 107.3 | 55.9 | 13.0 | 57.6 | 58.7 |
| LSD (0.05) | 3.0 | 4.66 | 0.6 | 17.03 | 5.7 | 5.633 |

TABLE 2

Comparison of flag leaf position, length and width and flag leaf sheath length of 'HB 329' and various Kentucky bluegrass varieties and HB 129 hybrid bluegrass for years 1 & 2.

| | | Length (mm) | | Width (mm) | | Sheath Length (cm) | |
|---|---|---|---|---|---|---|---|
| Variety | Position Year 1 | Year 1 | Year 2 | Year 1 | Year 2 | Year 1 | Year 2 |
| 'HB 329' | 2.1 | 54 | 75 | 3.3 | 3.3 | 10.7 | 14.0 |
| HB 129 | 1.4 | 60 | 73 | 3.8 | 3.3 | 13.2 | 15.4 |
| Moonshadow | 2.2 | 50 | 108 | 2.5 | 3.5 | 9.6 | 11.6 |
| America | 2.0 | 59 | 75 | 2.6 | 3.0 | 10.0 | 11.6 |
| Baron | 2.0 | 63 | 69 | 4.0 | 3.5 | 11.1 | 13.4 |
| Langara | 2.0 | 57 | 81 | 3.0 | 3.0 | 10.5 | 14.1 |
| Midnight | 2.0 | 74 | 86 | 3.4 | 3.2 | 10.7 | 11.4 |
| Touchdown | 1.6 | 60 | 81 | 3.5 | 3.6 | 12.9 | 16.4 |
| Adelphia | 1.5 | 53 | 79 | 3.3 | 3.2 | 10.7 | 13.4 |
| Ram I | 1.5 | 42 | 58 | 3.0 | 2.7 | 10.5 | 12.3 |
| Julia | 1.5 | 71 | 84 | 3.1 | 3.0 | 11.7 | 14.1 |
| Nugget | 1.4 | 29 | 41 | 2.2 | 2.1 | 7.4 | 9.0 |
| LSD (0.05) | 0.31 | 12.2 | 9.9 | 0.56 | 0.99 | 1.32 | 1.16 |

1 = Appressed
2 = Open Angle

TABLE 3

Comparison of panicle color, habit, branch attitude, branches in lowest whorl, length and collar for 'HB 329' and various Kentucky bluegrass varieties and HB 129 hybrid bluegrass for year 1.

| | Panicle Characteristics | | |
|---|---|---|---|
| Variety | Color | Habit | Branch Attitude |
| 'HB 329' | 1.9 | 1.8 | 2.9 |
| HB 129 | 2.0 | 1.9 | 2.9 |
| Touchdown | 2.0 | 1.9 | 2.4 |
| Baron | 1.9 | 1.9 | 2.7 |
| Midnight | 1.9 | 1.0 | 1.7 |
| Nugget | 1.8 | 1.8 | 3.0 |
| Ram I | 1.6 | 2.0 | 3.0 |

TABLE 3-continued

Comparison of panicle color, habit, branch attitude, branches in lowest whorl, length and collar for 'HB 329' and various Kentucky bluegrass varieties and HB 129 hybrid bluegrass for year 1.

| | | | |
|---|---|---|---|
| Adelphia | 1.4 | 2.0 | 1.4 |
| Langara | 1.3 | 1.0 | 2.7 |
| Julia | 1.3 | 1.0 | 1.0 |
| Moonshadow | 1.2 | 1.1 | 2.1 |
| America | 1.1 | 2.0 | 2.4 |
| LSD (0.05) | 0.23 | 0.24 | 0.24 |
| | 1 - not red<br>2 - red | 1 - nodding<br>2 - upright | 1 - drooping<br>2 - horizontal<br>3 - ascending |

| | Panicle Characteristics | | |
|---|---|---|---|
| Variety | Number of Branches in Lowest Whorl | Length (cm) | Collar |
| 'HB 329' | 4.1 | 9.5 | 1.0 |
| HB 129 | 4.40 | 10.6 | 1.0 |
| Touchdown | 3.82 | 10.4 | — |
| Baron | 4.72 | 10.6 | 1.0 |
| Midnight | 4.58 | 10.6 | 1.0 |
| Nugget | 2.80 | 6.3 | 1.1 |
| Ram I | 3.73 | 7.7 | 1.0 |
| Adelphia | 4.01 | 10.2 | 1.1 |
| Langara | 3.78 | 9.7 | 1.0 |
| Julia | 4.52 | 11.4 | 1.0 |
| Moonshadow | 4.49 | 9.4 | 1.0 |
| America | 4.07 | 8.8 | 1.0 |
| LSD (0.05) | 0.52 | 1.07 | 0.05 |
| | | | 1 - open<br>2 - closed. |

TABLE 4

Comparison of panicle color, habit, branch attitude, branches in lowest whorl, length, and collar for 'HB 329' and various Kentucky bluegrass varieties and HB 129 hybrid bluegrass for year 2.

| Variety | Color | Habit | Branch Attitude |
|---|---|---|---|
| 'HB 329' | 2.0 | 1.1 | 1.3 |
| HB 129 | 2.0 | 1.1 | 1.0 |
| Baron | 2.0 | 1.7 | 1.1 |
| Touchdown | 2.0 | 1.0 | 1.2 |
| Nugget | 1.9 | 1.0 | 1.5 |
| Midnight | 1.8 | 1.9 | 1.2 |
| Julia | 1.2 | 1.3 | 1.1 |
| Langara | 1.1 | 1.0 | 1.0 |
| Adelphia | 1.1 | 1.1 | 1.3 |
| Moonshadow | 1.0 | 1.1 | 1.0 |
| America | 1.0 | 2.0 | 1.0 |
| Ram I | 1.0 | 1.6 | 1.0 |
| LSD (0.05) | 0.2993 | 0.2553 | 0.3610 |
| | 1 = not red<br>2 = red | 1 = nodding<br>2 = upright | 1 = drooping<br>2 = horizontal<br>3 = ascending |

| Variety | Number of Branches in Lowest Whorl | Panicle Length (cm) | Collar |
|---|---|---|---|
| 'HB 329' | 4.4 | 10.0 | 1.0 |
| HB 129 | 4.4 | 11.0 | 1.0 |
| Baron | 4.8 | 10.2 | 1.1 |
| Touchdown | 3.9 | 12.5 | 1.0 |
| Nugget | 3.2 | 7.0 | 1.0 |
| Midnight | 4.4 | 9.9 | 1.8 |
| Julia | 4.2 | 11.4 | 1.2 |
| Langara | 4.3 | 12.6 | 1.2 |
| Adelphia | 4.2 | 12.3 | 1.6 |
| Moonshadow | 4.3 | 9.8 | 1.3 |
| America | 4.0 | 9.7 | 1.9 |

TABLE 4-continued

Comparison of panicle color, habit, branch attitude, branches in lowest whorl, length, and collar for 'HB 329' and various Kentucky bluegrass varieties and HB 129 hybrid bluegrass for year 2.

| | | | |
|---|---|---|---|
| Ram I | 4.3 | 8.5 | 1.0 |
| LSD (0.05) | 0.3899 | 1.578 | 0.3610 |
| | | | 1 = open<br>2 = closed |

TABLE 5

Comparison of panicle shape of rachis for 'HB 329' and various Kentucky bluegrass varieties and HB 129 hybrid bluegrass for years 1 & 2.

| | Panicle Shape | |
|---|---|---|
| Variety | Year 1 | Year 2 |
| 'HB 329' | 2.0 | 1.9 |
| HB 129 | 1.8 | 1.9 |
| Nugget | 2.0 | 1.3 |
| Adelphia | 1.9 | 1.7 |
| Ram I | 1.9 | 1.8 |
| Moonshadow | 1.4 | 1.9 |
| Baron | 1.2 | 1.9 |
| America | 1.2 | 1.7 |
| Langara | 1.1 | 1.8 |
| Touchdown | 1.1 | 1.5 |
| Midnight | 1.1 | 1.7 |
| Julia | 1.0 | 2.0 |
| LSD (0.05) | 0.117 | 0.255 |
| | 1 = no bend<br>2 = bend | 1 = no bend<br>2 = bend |

TABLE 6

Comparison of anther color of 'HB 329' and various Kentucky bluegrass varieties and HB 129 hybrid bluegrass for year 2.

| | Anther Color Categories (% of all anthers examined) | | |
|---|---|---|---|
| Variety | Purple | Yellow | Brown |
| 'HB 329' | 87 | 13 | 0 |
| HB 129 | 100 | 0 | 0 |
| Adelphia | 67 | 33 | 0 |
| America | 46 | 54 | 0 |
| Baron | 16 | 84 | 0 |
| Julia | 26 | 74 | 0 |
| Langara | 65 | 35 | 0 |
| Midnight | 98 | 2 | 0 |
| Nugget | 70 | 30 | 0 |
| Moonshadow | 9 | 91 | 0 |
| Ram I | 100 | 0 | 0 |
| Touchdown | 11 | 89 | 0 |

TABLE 7

Leaf sheath morphological traits of Kentucky bluegrass accessions measured 2002-2003 from the PVP nursery and greenhouse measurements at the research facility of Pickseed West, Inc. Oregon.

| Bluegrass Accessions | Keel | Hairs on Surface | Hairs on Both Sides Under Collar |
|---|---|---|---|
| 'HB 329' | 2 | 1 | 1 = 38% 2 = 62% |
| HB 129 | 2 | 1 | 1 = 8% 2 = 92% |
| America | 2 | 1 | 2 |
| Mercury | — | — | — |
| | 1 - absent<br>2 - present | 1 - absent<br>2 - present | 1 - absent<br>2 - present |

TABLE 7-continued

Leaf sheath morphological traits of Kentucky bluegrass accessions measured 2002-2003 from the PVP nursery and greenhouse measurements at the research facility of Pickseed West, Inc. Oregon.

| Bluegrass Accessions | Base of Sheath Color | Surface Roughness To Touch |
|---|---|---|
| 'HB 329' | 1 | 1 |
| HB 129 | 1 | 1 |
| America | 1 | 1 |
| Mercury | — | — |
| | 1 - green<br>2 - red | 1 - smooth<br>2 - rough |

TABLE 8

Leaf blade morphological traits of Kentucky bluegrass accessions measured 2002-2003 from the PVP nursery and greenhouse measurements at the research facility of Pickseed West, Inc. Oregon.

| Bluegrass Accessions | Margin Hairs | Hairs Upper Side | Hairs Lower Side |
|---|---|---|---|
| 'HB 329' | 2 | 1 = 77%<br>2 = 23% | 1 |
| HB 129 | 2 | 2 = 82%<br>1 = 18% | 1 |
| America | 2 | 1 | 1 |
| Mercury | — | — | — |
| | 1 - absent<br>2 - present | 1 - absent<br>2 - sparse<br>3 - dense | 1 - absent<br>2 - sparse<br>3 - dense |

| Bluegrass Accessions | Luster Upper Side | Luster Lower Side | Blade Width |
|---|---|---|---|
| 'HB 329' | 2 | 1 | 3 = 8%<br>4 = 92% |
| HB 129 | 2 | 1 | 5 |
| America | 2 | 1 | 2 |
| Mercury | — | — | — |
| | 1 - shiny<br>2 - dull | 1 - shiny<br>2 - dull | 1 - very fine<br>2 - fine<br>3 - medium<br>4 - broad<br>5 - very broad |

TABLE 9

Lemma morphological traits and seed phenol reaction of Kentucky bluegrass accessions measured 2002-2003 from the PVP nursery and greenhouse measurements at the research facility of Pickseed West, Inc. Oregon.

| | Lemma | | |
|---|---|---|---|
| Bluegrass Accessions | Keel | Marginal Nerves | Intermediate Nerves |
| 'HB 329' | 1 - 35%<br>2 - 55%<br>3 - 10% | 1 = 10%<br>2 = 90% | 1 = 5%<br>2 = 95% |
| HB 129 | 1 - 55%<br>2 - 45% | 1 - 30%<br>2 - 70% | 1 - 15%<br>2 - 85% |
| America | — | — | — |
| Mercury | 1 - 90%<br>2 - 10% | 2 | 2 |
| | 1 - glabrous<br>2 - slight pubescence<br>3 - pubescent | 1 - Yes<br>2 - No | 1 - distinct<br>2 - obscure |

TABLE 9-continued

Lemma morphological traits and seed phenol reaction of Kentucky bluegrass accessions measured 2002-2003 from the PVP nursery and greenhouse measurements at the research facility of Pickseed West, Inc. Oregon.

| Bluegrass Accessions | Lemma Basal Webbing | Seed Phenol Reaction |
|---|---|---|
| 'HB 329' | 1 = 70%<br>2 = 30% | 1 = 8%<br>3 = 92% |
| HB 129 | 1 - 90%<br>2 - 10% | 1 - 10%<br>2 - 90% |
| America | — | — |
| Mercury | 2 | 1 - 5%<br>2 - 95% |
| | 1 - absent<br>2 - scant<br>3 - copious | 1 - none<br>2 - beige<br>3 - brown<br>4 - black after 4 hrs<br>5 - black after 24 hrs |

TABLE 10

Plant spread, hairs on ligule and leaf sheath glaucosity of Kentucky bluegrass accessions measured 2002-2003 from the PVP nursery and greenhouse measurements at the research facility of Pickseed West, Inc. Oregon.

| Bluegrass Accessions | Amount of Spread in 1 year via Rhizomes (cm) | Hairs on Ligule | Leaf Sheath Glaucosity |
|---|---|---|---|
| 'HB 329' | 56 | 1 - 80%, 2 - 20% | 2 |
| HB 129 | 64 | 1 - 53% 2 - 47% | 2 |
| America | — | — | — |
| Mercury | 49 | 1 | 1 - 17%<br>2 - 83% |
| | | 1 - absent<br>2 - short<br>3 - long | 1 - absent<br>2 - present |

The seed of 'HB 329' was conditioned by removing most of the extraneous materials that may have been harvested with the seed, such as small pieces of plant stems and leaves, soil particles, seed of other plants and the like. This conditioned seed of 'HB 329' averages 3.16 mm in length, and 0.87 mm in width. 'HB 329' has about 789,565 seeds per pound.

Comparisons of 'HB 329' with 'HB 129' and Kentucky bluegrass varieties in terms of seed length, seed width and 1000 seed weight are shown in Table 11 as follows:

TABLE 11

Comparison of seed length, seed width and 1000 count seed weight of 'HB 329' and various Kentucky bluegrass varieties and HB 129 hybrid bluegrass for years 1 & 2.

| | Seed Length (mm) | Seed Width (mm) | 1000 Count Seed Weight (g) | |
|---|---|---|---|---|
| Variety | Year 1 | Year 1 | Year 1 | Year 2 |
| 'HB 329' | 3.16 | 0.87 | 0.633 | 0.517 |
| HB 129 | 2.75 | 0.97 | 0.657 | 0.423 |
| Touchdown | 3.00 | 0.92 | 0.753 | 0.417 |
| Baron | 2.87 | 0.97 | 0.690 | 0.467 |
| Ram I | 3.20 | 0.91 | 0.647 | 0.437 |
| Midnight | 3.03 | 0.81 | 0.637 | 0.403 |
| Julia | 2.82 | 0.82 | 0.630 | 0.507 |
| Langara | 2.77 | 0.80 | 0.573 | 0.463 |
| Adelphia | 2.90 | 0.83 | 0.560 | 0.340 |
| Moonshadow | 2.57 | 0.87 | 0.553 | 0.330 |
| Nugget | 3.22 | 0.90 | 0.543 | 0.200 |

TABLE 11-continued

Comparison of seed length, seed width and 1000 count seed weight of 'HB 329' and various Kentucky bluegrass varieties and HB 129 hybrid bluegrass for years 1 & 2.

| | Seed Length (mm) | Seed Width (mm) | 1000 Count Seed Weight (g) | |
|---|---|---|---|---|
| Variety | Year 1 | Year 1 | Year 1 | Year 2 |
| America | 2.63 | 0.83 | 0.470 | 0.383 |
| LSD (0.05) | 0.4 | 0.067 | 0.09 | 0.074 |

'HB 329' has shown reduced seed cotton on conditioned and unconditioned seed compared to Reveille and greater seed cotton compared to HB 129 (Tables 12 and 13). It is thought that the presence of the cotton on seed has led to poor seed recovery and the availability of Reveille predominantly as a vegetatively reproduced product from rhizome and tiller materials.

TABLE 12

Comparison of 'HB 329' to other hybrid bluegrasses for cotton on conditioned seed.

| Variety | Seed cotton rating<br>1 - no or little cotton, 2 - scant cotton, 3 - copious cotton |
|---|---|
| 'HB 329' | 2 |
| HB 129 | 1 |
| Reveille | 3 |

TABLE 13

Comparison of lemma length (eyepiece assisted), lemma cotton length (% of lemma length), lemma cotton length calculation and length of the cotton (eyepiece assisted, 7×) from spikelets harvested (unconditioned seed) from various bluegrass cultivars grown in a greenhouse under controlled environment (average 4 florets subsamples-lower whorl branches) at Gervais, Oregon. Data were collected from three replicates. 'HB 329' showed reduced lemma cotton length (column C) when compared to Reveille hybrid bluegrass and Texas 51-90 Texas bluegrass but greater than HB 129.

| Column<br>Variety | Lower Whorl Lemma Length Eyepiece (7×)<br>A<br>mm | Lemma Cotton Length (Visual) % of Lemma Length<br>B<br>Percent | Lower Whorl Lemma Cotton Length (Lemma Length × %) (A) × (B) = C<br>C<br>mm | Lower Whorl Lemma Cotton Length Eyepiece (7×)<br>D<br>mm |
|---|---|---|---|---|
| 'HB 329' | 4.8 | 61.1 | 2.9 | 3.1 |
| HB 129 | 3.9 | 49.1 | 1.9 | 1.8 |
| Texas 51-90 | 5.7 | 126.1 | 7.0 | 6.8 |
| Reveille | 4.4 | 94.2 | 4.1 | 4.1 |
| Ascot | 4.1 | 52.5 | 2.2 | 2.2 |
| Geronimo | 3.8 | 50.7 | 2.0 | 1.9 |
| LSD (P = 0.05) | 0.8 | 19.3 | 0.9 | 0.7 |
| CV | 10.7 | 15.8 | 16.2 | 12.2 |

'HB 329' has performed well throughout the U.S. as exhibited by good turf quality ratings under reduced management inputs in comparison with other Kentucky bluegrass varieties and other Texas×Kentucky bluegrass hybrids. In addition, it has a dark green color with moderate turf density that can be maintained throughout the growing season. 'HB 329' shows good fall and winter color compared with most Kentucky bluegrass varieties and HB 129 hybrid bluegrass.

TABLE 14

Comparison of 'HB 329' with Texas bluegrass and various Kentucky bluegrasses and HB 129 hybrid bluegrass.

| Variety | Plant Height (cm) | Longest Rhizome (cm) | Panicle Length (mm) | Flag Leaf Length (mm) | Flag Leaf Width (mm) | Flag Leaf Sheath Length (mm) |
|---|---|---|---|---|---|---|
| 'HB 329' | 27.3 | 38.0 | 63.5 | 31.2 | 3.9 | 53.7 |
| HB 129 | 41.5 | 49.0 | 25.6 | 25.6 | 4.0 | 74.3 |
| Unique | 17.3 | 40.0 | 34.7 | 14.2 | 1.2 | 48.5 |
| Abbey | 37.0 | 44.0 | 62.8 | 21.1 | 3.5 | 76.3 |
| Texas bluegrass | 80.0 | 53.3 | 126.9 | 97.2 | 6.4 | 146.9 |
| Midnight | 21.8 | 36.6 | — | — | — | — |
| Touchdown | 39.8 | 50.0 | 27.4 | 27.4 | 3.6 | 66.5 |
| Limousine | 29.8 | 40.8 | 18.9 | 18.9 | 3.2 | 52.5 |
| LSD (0.05) | 14.0 | 9.8 | 22.2 | 15.0 | 0.5 | 25.8 |

'HB 329' bluegrass has been shown to provide good downy mildew tolerance, good melting out disease tolerance, dark green genetic color and above average winter color (Table 15). 'HB 329' bluegrass has been shown to possess good living ground cover in the summer, medium leaf texture and average spring greenup as compared to other bluegrasses (Table 16).

TABLE 15

Differences between 'HB 329' and other Grasses in the 2001, 2002, and 2003 Reports of the National Kentucky Bluegrass Evaluation Program. (For definition of x and o' see bottom of table.)

| | Melting Out Disease Rating | Melting Out Disease Rating | Downy Mildew Rating | Winter Color Rating |
|---|---|---|---|---|
| | | Locations | | |
| | 2 | PA | WA | 4 |
| | | Year | | |
| Genptype/Cultivar | 2001 | 2003 | 2003 | 2003 |
| 'HB 329' | | | | |
| IB7-308 | | | o | |
| 99AN-53 | | o | o | o |
| A96-427 | | | o | o |
| A96-451 | | | o | o |
| A96-739 | | | | |
| A96-742 | o | o | | |
| A97-1330 | | o | o | o |
| A97-1409 | | | o | o |
| A91-1432 | | | o | o |
| A97-1715 | | | | o |
| A97-857 | | o | | |
| A98-1028 | o | | | o |
| A98-139 | | o | | |
| A98-183 | | | | |
| A98-365 | | | o | o |
| A98-407 | | | o | o |
| A98-881 | o | | | |
| Abbey | o | | | |
| Allure | o | | o | o |
| Alpine | o | | | o |
| Apollo | | | o | o |
| Arcadia | | | | o |
| Arrow (A97-1567) | | | o | o |
| Ascot | | | o | o |
| AVALANCHE (PST-1701) | | o | o | o |
| Award | | o | | o |
| Awesome (J-1420) | | | | o |
| B3-171 | | | o | o |
| B3-185 | | | o | o |

TABLE 15-continued

Differences between 'HB 329' and other Grasses in the 2001, 2002, and 2003 Reports of the National Kentucky Bluegrass Evaluation Program. (For definition of x and o' see bottom of table.)

| | | | | |
|---|---|---|---|---|
| B4-128A | | | o | o |
| B5-144 | o | o | o | o |
| B5-43 | o | o | o | o |
| B5-45 | o | | o | o |
| Ba 00-6001 | | | o | o |
| Ba 82-288 | | | | |
| Ba 83-113 | | | o | o |
| Ba 84-140 | | | o | |
| BAR Pp 0468 | | | o | o |
| BAR Pp 0471 | | | o | o |
| BAR Pp 0566 | | | | |
| BAR Pp 0573 | | | o | o |
| Bariris | o | | | o |
| Baritone | o | | | o |
| Baron | | | | o |
| Baronette (Ba 81-058) | | | | |
| Baronle | o | | o | o |
| Barrister (J-1655) | o | | | o |
| Bartitia | o | | | o |
| Barzan | | o | | o |
| Bedazzled | | | o | |
| Beyond (J-1880) | | | | o |
| BH 00-6002 (HB 129) | o | o | o | o |
| Blacksburg II (PST-1BMY) | | | | |
| Blackstone | | o | | |
| Blue Knight | o | o | o | o |
| Blue Ridge (A97-1449) | | | o | o |
| Blue Sapphire (NA-K991) | | | | |
| Bluemax (PST-B5-89) | | | | |
| Bluestone (PST-731) | | o | | o |
| Bodacious | o | | | |
| Boomerang | | | o | o |
| Bordeaux | | | o | o |
| Boutique | | | o | |
| Brilliant | | | o | o |
| Brooklawn | o | o | o | o |
| Cabernet | | o | | |
| Champagne | | | | |
| Champlain (A98-1275) | | | o | o |
| Chateau | o | | o | o |
| Chelsea | | o | o | o |
| Chicago II | | | | o |
| Coventry | o | | o | o |
| CVB-20631 | o | | | o |
| DLF 76-9032 | | | o | o |
| DLF 76-9034 | | o | | o |
| DLF 76-9036 | o | | | o |
| DLF 76-9037 | | | o | o |
| Eagleton | o | o | | o |
| Envicta | o | | | o |
| Everest | o | | | o |
| EverGlade | o | | o | o |
| Excursion (J-1648) | o | | o | o |
| Fairfax | o | | o | o |
| Freedom II | | | | o |
| Ginney (J-1368) | o | | | o |
| Glenmont (H94-293) | | | | |
| GO-9LM9 | o | o | | |
| Goldrush | o | | | o |
| Goldstar (A98-296) | | | o | o |
| H92-203 | | | o | o |
| H92-558 | | | o | o |
| Hallmark | o | | o | o |
| HV 140 | o | o | o | o |
| HV-238 | | | | |

TABLE 15-continued

Differences between 'HB 329' and other Grasses in the 2001, 2002, and 2003 Reports of the National Kentucky Bluegrass Evaluation Program. (For definition of x and o' see bottom of table.)

| | | | | |
|---|---|---|---|---|
| Impact | | | | o |
| J-1513 | o | | o | o |
| J-1838 | o | | o | o |
| J-2561 | o | | | o |
| J-2885 | | | | |
| J-2890 | o | | | o |
| Jefferson | | | o | o |
| Jewel | o | o | o | o |
| Julia | o | o | | |
| Julius | o | | | o |
| Kenblue | o | o | | o |
| Lakeshore | | | | o |
| (A93-200) | | | | |
| Langara | | | | |
| Liberator | | o | | o |
| Lily | o | | o | o |
| Limerick | | | | o |
| Limousine | | | o | o |
| Mallard (A97-1439) | | | o | o |
| Markham | o | | o | o |
| (NA-K991) | | | | |
| Marquis | | | o | o |
| Mercury (Pick-232) | | o | | o |
| Midnight | | | | o |
| Midnight II | | | o | o |
| (A98-739) | | | | |
| Misty | | o | o | o |
| Monte Carlo | | | | o |
| (A96-402) | | | | |
| Moon Shadow | | o | | o |
| (Pick 113-3) | | | | |
| Moonlight | | | | |
| NA-K992 | o | o | | |
| North Star | o | | o | o |
| NU Destiny | | o | | o |
| (J-2695) | | | | |
| NuGlade | | | o | o |
| Odyssey | | o | | |
| Perfection (J-1515) | | | | o |
| Pick 417 | | | o | o |
| Pick 453 | | | o | o |
| Pp H 6366 | | | | o |
| Pp H 6370 | o | o | | |
| Pp H 7832 | | | | |
| Pp H 7907 | | | | |
| Pp H 7929 | | | | o |
| Princeton 105 | o | | o | o |
| Pro Seeds - 453 | | | | o |
| PST-108-79 | o | | | o |
| PST-161 | | o | | |
| PST-1804 | | | | o |
| PST-222 | | | o | o |
| PST-604 | | | o | |
| PST-B3-170 | | | o | o |
| PST-B4-246 | | | o | o |
| PST-B5-125 | | | o | o |
| PST-H5-35 | | | o | o |
| PST-H6-150 | | | o | o |
| PST-York Harbor 4 | o | | o | o |
| Quantum Leap | o | | | o |
| Rambo | | | o | o |
| Raven | o | | | o |
| Rita | | | o | |
| Royale (A97-1336) | | | o | o |
| Royce (A98-304) | | | o | o |
| Rugby II | o | | | o |
| Serene | o | o | o | o |
| Shamrock | | | | |
| Showcase | | | o | o |
| SI A96-386 | | | | |
| Sonoma | | | o | o |
| SR 2284 | | | | |
| (SRX 2284) | | | | |
| SRX 2114 | | | o | o |

TABLE 15-continued

Differences between 'HB 329' and other Grasses in the 2001, 2002, and 2003 Reports of the National Kentucky Bluegrass Evaluation Program. (For definition of x and o' see bottom of table.)

| | | | | |
|---|---|---|---|---|
| SRX 2394 | | | | |
| SRX 26351 | | | | o |
| SRX 27921 | | | | o |
| SRX QG245 | o | o | o | o |
| Total Eclipse | o | | | o |
| Tsunami (J-2487) | o | | o | o |
| Unique | | | o | o |
| Unknown | | | | o |
| Voyager II | | | o | o |
| (PST-1QG-27) | | | | |
| Washington | o | o | | o |
| Wellington | o | o | | |
| Wildwood | o | | o | o |

| | Winter Color Rating | Winter Color Rating | Genetic Color Rating Locations | Genetic Color Rating | Genetic Color Rating |
|---|---|---|---|---|---|
| | 5 | 3 | 24 | 27 | 14 |
| | | | Year | | |
| Genptype/Cultivar | 2002 | 2001 | 2003 | 2001 | 2002 |
| 'HB 329' | | | | | |
| IB7-308 | | | x | x | x |
| 99AN-53 | | | o | o | o |
| A96-427 | | | | o | |
| A96-451 | | | x | | x |
| A96-739 | | | | | |
| A96-742 | | o | o | o | o |
| A97-1330 | o | o | o | o | o |
| A97-1409 | x | x | x | | x |
| A91-1432 | | | | | |
| A97-1715 | | o | | o | o |
| A97-857 | | | o | o | o |
| A98-1028 | x | | o | o | o |
| A98-139 | x | | o | o | o |
| A98-183 | | | | | |
| A98-365 | o | | | | x |
| A98-407 | | | | | |
| A98-881 | | | o | o | o |
| Abbey | | o | o | o | o |
| Allure | o | | o | o | o |
| Alpine | | o | o | o | o |
| Apollo | | o | o | o | o |
| Arcadia | | o | x | | x |
| Arrow (A97-1567) | | | | o | |
| Ascot | | o | | o | |
| AVALANCHE | | o | o | o | o |
| (PST-1701) | | | | | |
| Award | | o | x | x | x |
| Awesome (J-1420) | | | x | | x |
| B3-171 | | o | o | o | o |
| B3-185 | o | o | o | o | o |
| B4-128A | | o | o | o | o |
| B5-144 | | o | o | o | o |
| B5-43 | o | o | o | o | o |
| B5-45 | o | o | o | o | o |
| Ba 00-6001 | o | o | | | |
| Ba 82-288 | x | | | o | |
| Ba 83-113 | x | | | | |
| Ba 84-140 | | o | x | x | x |
| BAR Pp 0468 | | o | o | o | o |
| BAR Pp 0471 | o | o | o | o | o |
| BAR Pp 0566 | | | x | | |
| BAR Pp 0573 | | | | o | |
| Bariris | | o | o | o | o |
| Baritone | | | o | o | o |
| Baron | o | o | o | o | o |
| Baronette | | x | | o | |
| (Ba 81-058) | | | | | |
| Baronle | | | o | o | o |
| Barrister (J-1655) | | | x | | x |

TABLE 15-continued

Differences between 'HB 329' and other Grasses in the 2001, 2002, and 2003 Reports of the National Kentucky Bluegrass Evaluation Program. (For definition of x and o' see bottom of table.)

| | | | | | |
|---|---|---|---|---|---|
| Bartitia | | o | o | o | o |
| Barzan | x | | o | o | o |
| Bedazzled | | | | o | |
| Beyond (J-1880) | | | x | | x |
| BH 00-6002 | o | o | o | o | o |
| (HB 129) | | | | | |
| Blacksburg II | | | | | |
| (PST-1BMY) | | | | | |
| Blackstone | x | | x | | |
| Blue Knight | | | x | | |
| Blue Ridge | | | x | x | x |
| (A97-1449) | | | | | |
| Blue Sapphire | | | | | |
| (NA-K991) | | | | | |
| Bluemax | | | x | x | x |
| (PST-B5-89) | | | | | |
| Bluestone | | | x | | x |
| (PST-731) | | | | | |
| Bodacious | | o | | | |
| Boomerang | | o | | | x |
| Bordeaux | | | x | | x |
| Boutique | | | | | x |
| Brilliant | o | o | o | o | o |
| Brooklawn | | o | o | o | o |
| Cabernet | | o | o | o | o |
| Champagne | | | o | o | o |
| Champlain | | o | | o | |
| (A98-1275) | | | | | |
| Chateau | | o | o | o | o |
| Chelsea | | o | o | o | o |
| Chicago II | | | x | x | x |
| Coventry | o | o | o | o | o |
| CVB-20631 | o | | o | o | o |
| DLF 76-9032 | o | o | o | o | o |
| DLF 76-9034 | o | o | o | o | o |
| DLF 76-9036 | | o | o | o | o |
| DLF 76-9037 | o | o | o | o | o |
| Eagleton | | o | o | o | o |
| Envicta | | o | o | o | o |
| Everest | | o | x | | x |
| EverGlade | | o | x | | x |
| Excursion (J-1648) | | | x | | x |
| Fairfax | o | o | o | o | o |
| Freedom II | | | x | | x |
| Ginney (J-1368) | | | x | | x |
| Glenmont | | | | o | |
| (H94-293) | | | | | |
| GO-9LM9 | | o | o | o | o |
| Goldrush | | o | o | o | o |
| Goldstar (A98-296) | | | | o | |
| H92-203 | o | o | o | o | o |
| H92-558 | | | x | o | |
| Hallmark | | o | | o | |
| HV 140 | o | o | o | o | o |
| HV-238 | | | o | o | o |
| Impact | | | x | | x |
| J-1513 | | o | x | x | x |
| J-1838 | | o | x | | x |
| J-2561 | | | x | | x |
| J-2885 | | | x | | x |
| J-2890 | | | x | | x |
| Jefferson | | | o | o | o |
| Jewel | o | o | o | o | o |
| Julia | | | o | o | o |
| Julius | | o | o | o | o |
| Kenblue | o | o | o | o | o |
| Lakeshore | | o | o | o | o |
| (A93-200) | | | | | |
| Langara | | | | o | o |
| Liberator | | o | | | x |
| Lily | | | o | o | o |
| Limerick | o | o | o | o | o |
| Limousine | | o | o | o | o |
| Mallard (A97-1439) | | | | | |

TABLE 15-continued

Differences between 'HB 329' and other Grasses in the 2001, 2002, and 2003 Reports of the National Kentucky Bluegrass Evaluation Program. (For definition of x and o' see bottom of table.)

| | | | | | |
|---|---|---|---|---|---|
| Markham | x | | o | | x |
| (NA-K991) | | | | | |
| Marquis | | o | o | o | o |
| Mercury (Pick-232) | o | o | | | |
| Midnight | | | x | | x |
| Midnight II | | o | x | | x |
| (A98-739) | | | | | |
| Misty | x | | o | o | o |
| Monte Carlo | | | | | |
| (A96-402) | | | | | |
| Moon Shadow | | | | | |
| (Pick 113-3) | | | | | |
| Moonlight | | | o | x | x |
| NA-K992 | o | o | x | | |
| North Star | | o | | o | |
| NU Destiny | | o | x | | x |
| (J-2695) | | | | | |
| NuGlade | | o | x | | x |
| Odyssey | | o | x | | x |
| Perfection | | | x | | x |
| (J-1515) | | | | | |
| Pick 417 | | o | x | o | |
| Pick 453 | | o | | o | |
| Pp H 6366 | | o | o | o | o |
| Pp H 6370 | | | o | o | o |
| Pp H 7832 | | | | o | o |
| Pp H 7907 | | o | | o | |
| Pp H 7929 | | o | o | o | o |
| Princeton 105 | | o | | o | |
| Pro Seeds - 453 | o | o | o | o | |
| PST-108-79 | | | o | o | o |
| PST-161 | | | | o | o |
| PST-1804 | | o | o | o | o |
| PST-222 | | | x | x | x |
| PST-1804 | | | | | |
| PST-83-170 | | | | o | |
| PST-84-246 | | o | | o | |
| PST-85-125 | | | | o | |
| PST-H5-35 | | | | o | |
| PST-H6-150 | o | o | o | o | o |
| PST-York Harbor 4 | | | | o | |
| Quantum Leap | | | x | x | x |
| Rambo | | o | o | o | o |
| Raven | | o | o | o | o |
| Rita | x | | | o | |
| Royale (A97-1336) | | | | o | o |
| Royce (A98-304) | o | o | o | o | o |
| Rugby II | | o | x | | x |
| Serene | | | o | o | o |
| Shamrock | | | o | o | o |
| Showcase | o | o | o | o | o |
| SI A96-386 | | | | o | |
| Sonoma | | | | o | |
| SR 2284 | | | | o | |
| (SRX 2284) | | | | | |
| SRX 2114 | | | x | o | x |
| SRX 2394 | | | x | | |
| SRX 26351 | | | | o | |
| SRX 27921 | | o | | | |
| SRX QG245 | | | | o | o |
| Total Eclipse | | | x | | x |
| Tsunami (J-2467) | | o | x | | x |
| Unique | o | o | o | o | o |
| Unknown | | | x | | x |
| Voyager II | o | o | o | o | o |
| (PST-1QG-27) | | | | | |
| Washington | | o | o | o | o |
| Wellington | | o | o | o | o |
| Wildwood | | | | o | |

o Denotes significanty lesser or poorer performance than ('HB 329') based on LSD Values
x Denotes significantly greater or better performance than ('HB 329') based on LSD Values
Denotes similiar performance to ('HB 329') based on LSD Values

TABLE 16

Differences between 'HB 329' and other Grasses in the 2001, 2002, and 2003 Reports of the National Kentucky Bluegrass Evaluation Program. (For definition of x and o' see bottom of table.)

| Genotype/ Cultivar | % Living Ground Cover Summer | % Living Ground Cover Summer | Leaf Texture Rating | Leaf Texture Rating | Spring Green Up Rating | Spring Green Up Rating |
|---|---|---|---|---|---|---|
| | Locations | | | | | |
| | 6 | 3 | 18 | 21 | 21 | 21 |
| | Year | | | | | |
| | 2002 | 2003 | 2002 | 2003 | 2002 | 2003 |
| 'HB 329' | | | | | | |
| IB7-308 | | | x | x | | o |
| 99AN-53 | o | o | | x | | |
| A96-427 | | | x | | x | x |
| A96-451 | o | o | x | | x | |
| A96-739 | | | x | x | x | x |
| A96-742 | o | | x | x | x | x |
| A97-1330 | | | x | | | |
| A97-1409 | o | o | x | | x | |
| A97-1432 | | | x | x | x | x |
| A97-1715 | | | x | x | x | x |
| A97-857 | | | x | | | x |
| A98-1028 | | | x | | x | x |
| A98-139 | | | x | x | x | x |
| A98-183 | | | x | x | | |
| A98-365 | | | x | | | |
| A98-407 | o | o | | | x | |
| A98-881 | | o | x | x | x | x |
| Abbey | | | | x | x | |
| Allure | | o | | | | |
| Alpine | o | | x | | o | o |
| Apollo | | | x | x | | |
| Arcadia | o | | x | x | o | o |
| Arrow (A97-1567) | | | x | | x | |
| Ascot | | | x | | o | o |
| AVALANCHE (PST-1701) | | | x | x | x | x |
| Award | | | x | x | o | o |
| Awesome (J-1420) | o | | x | | | o |
| B3-171 | | | x | | | |
| B3-185 | | x | x | x | | |
| B4-128A | o | | x | x | | |
| B5-144 | | | | | | |
| B5-43 | | | | | x | |
| B5-45 | | | | x | | |
| Ba 00-6001 | o | | x | x | | o |
| Ba 82-288 | o | | x | | x | x |
| Ba 83-113 | | | x | | x | x |
| Ba 84-140 | o | o | x | x | | |
| BAR Pp 0468 | | | x | x | | |
| BAR Pp 0471 | | | x | | | |
| BAR Pp 0566 | o | | x | | x | x |
| BAR Pp 0573 | | | x | x | x | |
| Bariris | o | | x | x | | x |
| Baritone | | | x | | | |
| Baron | | o | x | | | |
| Baronette (Ba 81-058) | | | x | x | x | x |
| Baronie | | | x | x | x | x |
| Barrister (J-1655) | | | x | | | o |
| Bartitia | | o | x | | | |
| Barzan | | | x | x | o | o |
| Bedazzled | | | x | x | x | x |
| Beyond (J-1880) | | | x | | | o |
| BH 00-6002 (HB 129) | | | | | x | x |
| Blacksburg II (PST-1BMY) | | | x | x | x | x |

TABLE 16-continued

Differences between 'HB 329' and other Grasses in the 2001, 2002, and 2003 Reports of the National Kentucky Bluegrass Evaluation Program. (For definition of x and o' see bottom of table.)

| Genotype/ Cultivar | % Living Ground Cover Summer | % Living Ground Cover Summer | Leaf Texture Rating | Leaf Texture Rating | Spring Green Up Rating | Spring Green Up Rating |
|---|---|---|---|---|---|---|
| | Locations | | | | | |
| | 6 | 3 | 18 | 21 | 21 | 21 |
| | Year | | | | | |
| | 2002 | 2003 | 2002 | 2003 | 2002 | 2003 |
| Blackstone | | | x | x | x | x |
| Blue Knight | | o | x | | | o |
| Blue Ridge (A97-1449) | o | o | | | x | |
| Blue Sapphire (NA-K991) | | | | x | | |
| Bluemax (PST-B5-89) | | | x | x | | |
| Bluestone (PST-731) | | | x | | | o |
| Bodacious | o | o | x | | | |
| Boomerang | o | | x | x | | o |
| Bordeaux | o | | x | x | x | |
| Boutique | | | x | | x | x |
| Brilliant | | | x | | | |
| Brooklawn | | | x | x | x | x |
| Cabernet | | | x | x | | x |
| Champagne | o | | x | | x | x |
| Champlain (A98-1275) | | | x | | | o |
| Chateau | | | | x | | |
| Chelsea | o | | x | x | | o |
| Chicago II | | | x | | | |
| Coventry | o | | | | | |
| CVB-20631 | o | o | x | x | o | o |
| DLF 76-9032 | | | x | x | | |
| DLF 76-9034 | | | | | | o |
| DLF 76-9036 | | o | x | | | |
| DLF 76-9037 | | | x | x | | |
| Eagleton | | | x | x | | x |
| Envicta | o | o | | | | |
| Everest | o | | x | | o | o |
| EverGlade | o | | x | x | o | o |
| Excursion (J-1648) | o | | x | x | o | o |
| Fairfax | | | | | | |
| Freedom II | o | | x | | | |
| Ginney (J-1368) | | | x | x | o | o |
| Glenmont (H94-293) | | | x | x | x | |
| GO-9LM9 | o | o | x | | | x |
| Goldrush | | | x | | | |
| Goldstar (A98-296) | | | x | x | x | x |
| H92-203 | | | x | x | | |
| H92-558 | o | | x | | | |
| Hallmark | | | x | | | o |
| HV 140 | | | x | x | | |
| HV-238 | | | x | x | | x |
| Impact | o | | x | | o | o |
| J-1513 | o | | x | | o | o |
| J-1838 | o | | x | x | o | o |
| J-2561 | o | | x | x | o | o |
| J-2885 | | | x | | | |
| J-2890 | | | x | | o | o |
| Jefferson | o | | x | x | x | x |
| Jewel | | | x | x | | |
| Julia | o | | x | | | x |
| Julius | o | o | x | | | |
| Kenblue | | | x | x | | x |
| Lakeshore | | | x | x | x | x |

TABLE 16-continued

Differences between 'HB 329' and other Grasses in the 2001, 2002, and 2003 Reports of the National Kentucky Bluegrass Evaluation Program. (For definition of x and o' see bottom of table.)

| Genotype/ Cultivar | % Living Ground Cover Summer | % Living Ground Cover Summer | Leaf Texture Rating | Leaf Texture Rating | Spring Green Up Rating | Spring Green Up Rating |
|---|---|---|---|---|---|---|
| | Locations | | | | | |
| | 6 | 3 | 18 | 21 | 21 | 21 |
| | Year | | | | | |
| | 2002 | 2003 | 2002 | 2003 | 2002 | 2003 |
| (A92-200) | | | | | | |
| Langara | | | x | | x | x |
| Liberator | | | x | | | |
| Lily | | | | x | | |
| Limerick | o | | x | x | o | o |
| Limousine | | | x | | | x |
| Mallard | | | x | | | |
| (A97-1439) | | | | | | |
| Markham | o | | | x | | o |
| (NA-K991) | | | | | | |
| Marquis | | o | | x | | |
| Mercury | o | | x | | | |
| (Pick-232) | | | | | | |
| Midnight | | | x | | o | |
| Midnight II | | | x | x | o | o |
| (A98-739) | | | | | | |
| Misty | | | | x | | |
| Monte Carlo | | | | | x | |
| (A96-402) | | | | | | |
| Moon Shadow | | | x | | | |
| (Pick 113-3) | | | | | | |
| Moonlight | | | | x | x | |
| NA-K992 | o | | x | x | | |
| North Star | o | | x | | o | o |
| NU Destiny | | | x | | o | o |
| (J-2695) | | | | | | |
| NuGlade | | | x | x | | o |
| Odyssey | o | | x | x | o | o |
| Perfection | o | | x | | o | o |
| (J-1515) | | | | | | |
| Pick 417 | o | o | | | | |
| Pick 453 | o | | x | | | |
| Pp H 6366 | o | o | x | x | | |
| Pp H 6370 | o | | x | | x | |
| Pp H 7832 | | o | x | | | |
| Pp H 7907 | o | o | x | x | | |
| Pp H 7929 | o | o | x | x | | |
| Princeton 105 | | | x | | | o |
| Pro Seeds - 453 | | | x | | x | |
| PST-108-79 | | | x | x | | |
| PST-161 | | | x | x | x | x |
| PST-1804 | | | x | | x | x |
| PST-222 | o | o | | | | |
| PST-604 | | | x | x | x | x |
| PST-B3-170 | | | x | x | o | o |
| PST-B4-246 | | | x | | | o |
| PST-B5-125 | | | x | | | |
| PST-H5-35 | o | | x | x | | |
| PST-H6-150 | | | x | x | | |
| PST-York | | o | x | | | |
| Harbor 4 | | | | | | |
| Quantum Leap | | | x | | o | o |
| Rambo | o | | x | x | | |
| Raven | o | o | | x | | |
| Rita | | | x | | x | x |
| Royale | | o | x | | x | |
| (A97-1336) | | | | | | |
| Royce | | | x | x | | |
| (A98-304) | | | | | | |
| Rugby II | | | x | x | | o |
| Serene | | | x | | | |
| Shamrock | | | x | | x | x |

TABLE 16-continued

Differences between 'HB 329' and other Grasses in the 2001, 2002, and 2003 Reports of the National Kentucky Bluegrass Evaluation Program. (For definition of x and o' see bottom of table.)

| Genotype/ Cultivar | % Living Ground Cover Summer | % Living Ground Cover Summer | Leaf Texture Rating | Leaf Texture Rating | Spring Green Up Rating | Spring Green Up Rating |
|---|---|---|---|---|---|---|
| | Locations | | | | | |
| | 6 | 3 | 18 | 21 | 21 | 21 |
| | Year | | | | | |
| | 2002 | 2003 | 2002 | 2003 | 2002 | 2003 |
| Showcase | | | x | x | | |
| SI A96-386 | o | o | x | x | | |
| Sonoma | o | o | x | | x | |
| SR 2284 | o | | x | | x | x |
| (SRX 2284) | | | | | | |
| SRX 2114 | | | x | x | | o |
| SRX 2394 | o | o | x | x | x | o |
| SRX 26351 | o | o | x | | x | |
| SRX 27921 | o | o | x | | | o |
| SRX QG245 | o | o | x | x | x | x |
| Total Eclipse | | | x | x | | o |
| Tsunami | o | | x | | o | o |
| (J-2487) | | | | | | |
| Unique | | | x | | | |
| Unknown | | | x | x | o | o |
| Voyager II | | | x | x | | |
| (PST-1QG-27) | | | | | | |
| Washington | o | | x | | x | x |
| Wellington | | | x | | x | x |
| Wildwood | | | x | x | | |

o Denotes significantly lesser or poorer performance than ('HB 329') based on LSD Values
x Denotes significantly greater or better performance than ('HB 329') based on LSD Values
Denotes similar or comparable performance to ('HB 329') based on LSD Values With regard to a comparative analysis conducted for purposes of determining color of 'HB 329' plants relative to Kentucky bluegrass varieties and a hybrid bluegrass, readings were taken of the vegetative color of 'HB 329' on actively growing plants with adequate nutrient and water availability. Color readings showed that 'HB 329' leaves had a dark green color and has blue-green coloration. This was dissimilar to HB 129 and most Kentucky bluegrasses with the exception of Langara (Table 17).

TABLE 17

Comparison of ratings for growth habit, leaf color and leaf blade width for 'HB 329' and various Kentucky bluegrass varieties and HB 129 hybrid bluegrass for year 2.

| Variety | Growth Habit | Leaf Color: Green | Leaf Color: Blue Green | Blade Width |
|---|---|---|---|---|
| 'HB 329' | 2.0 | 3.6 | 3.1 | 2.7 |
| HB 129 | 2.0 | 1.0 | 1.0 | 4.5 |
| Langara | 3.0 | 3.1 | 1.9 | 3.6 |
| Julia | 2.1 | 1.6 | 1.4 | 3.2 |
| Adelphia | 2.0 | 2.4 | 1.8 | 4.0 |
| Touchdown | 1.9 | 1.0 | 1.0 | 4.9 |
| America | 1.9 | 2.8 | 2.3 | 3.1 |
| Midnight | 1.3 | 3.1 | 1.5 | 2.7 |
| Baron | 1.3 | 1.2 | 1.4 | 4.8 |
| Ram I | 1.2 | 2.0 | 1.0 | 3.9 |
| Nugget | 1.1 | 2.5 | 1.7 | 2.8 |
| LSD (0.05) | 0.4201 | 0.3899 | 0.5288 | 0.5025 |
| | 1 - Prostrate | 1 - Light Green | 1 - Not Blue Green | 1 - Very Fine |

TABLE 17-continued

Comparison of ratings for growth habit, leaf color and leaf blade width for 'HB 329' and various Kentucky bluegrass varieties and HB 129 hybrid bluegrass for year 2.

| Variety | Growth Habit | Leaf Color: Green | Leaf Color: Blue Green | Blade Width |
|---|---|---|---|---|
| | 2 - Semi-Prostrate<br>3 - Erect | 2 - Medium Green<br>3 - Mod Dark Green<br>4 - Very Dark Green | 2 - Mod Blue Green<br>3 - Blue-Green<br>4 - Strong Blue-Green | 2 - Fine<br>3 - Medium<br>4 - Broad<br>5 - Very Broad |

Further comparative testing of 'HB 329' plants relative to Kentucky bluegrass, Texas bluegrass and hybrid varieties was conducted and the results of this testing are set forth in the following Tables 18 and 19:

TABLE 18

Comparison of morphological traits of flowering tillers of plants allowed to over winter in the field and brought into a controlled greenhouse environment (60-75° F.) in late winter and allowed to grow undisturbed during the winter of 2004-2005 at The Scotts Company facility at Gervais, Oregon.

| Variety | Flag Leaf Ligule Length (mm) | Flag Leaf Ligule Hairs 0 = none 9 = Many | Flag Leaf Thickness (mm) | Anthesis (days to flowering) |
|---|---|---|---|---|
| 'HB 329' | 2.3 | 3.2 | 0.0182 | 145 |
| HB 129 | 1.3 | 5.8 | 0.0149 | 138 |
| Reveille | 2.3 | 0.9 | 0.0207 | 141 |
| Geronimo | 1.7 | 7.1 | 0.0164 | 140 |
| Ascot | 2.0 | 5.6 | 0.0166 | 141 |
| Midnight | 0.8 | 3.9 | 0.0145 | 148 |
| Buckingham | 2.4 | 8.1 | 0.0190 | 142 |
| Texas Bluegrass (TX 51-90) | 1.7 | 0.1 | 0.0262 | 140 |
| Texas Bluegrass (TX 39-88) | 2.7 | 0.1 | 0.0199 | |
| Texas Bluegrass (TX 49-90) | 2.0 | 0.5 | 0.0231 | 140 |
| Kelly | 2.1 | 6.3 | 0.0163 | 143 |
| LSD (P = .05) | 0.663 | 1.93 | 0.003324 | 4.854 |

'HB 329' has a similar flag leaf ligule, more hairs on the flag leaf ligule and a thinner flag leaf than Reveille hybrid bluegrass. 'HB 329' has a longer flag leaf ligule, fewer hairs on the flag leaf ligule and a thicker flag leaf than HB129 hybrid bluegrass (Table 18).

'HB 329' has a shorter spikelet length and fewer florets/spikelets on both the first whorl and third whorl than HB 129 hybrid bluegrass and is similar to Reveille hybrid bluegrass in these traits (Table 17). 'HB 329' has longer glumes than HB 129 and Reveille hybrid bluegrass. 'HB 329' is shorter than Reveille and HB 129 hybrid bluegrasses (Table 19).

TABLE 19

Comparison of morphological traits of plant inflorescence - spikelets, florets, glumes - from panicles havested from a field nursery and plant height in 2005 at The Scotts Company facility at Gervais, Oregon.

| Variety | Spikelet Length 1stWhorl (mm) | Spikelet Length 3rdWhorl (mm) | Spikelet Width 1stWhorl (mm) | Spikelet Width 3rdWhorl (mm) |
|---|---|---|---|---|
| 'HB 329' | 6.2 | 6.5 | 4.3 | 3.8 |
| HB 129 | 7.6 | 7.1 | 4.5 | 4.0 |
| Reveille | 6.1 | 6.4 | 4.0 | 4.2 |
| Geronimo | 5.5 | 6.3 | 4.2 | 4.0 |
| Ascot | 5.6 | 5.8 | 4.4 | 4.3 |
| Midnight | 5.7 | 6.4 | 2.7 | 3.2 |
| Buckingham | 6.9 | 6.9 | 4.6 | 4.7 |
| Texas Bluegrass TX 51-90 | 7.6 | 7.5 | 7.3 | 7.1 |
| Texas Bluegrass TX 39-88 | 8.6 | 8.5 | 5.9 | 5.7 |
| Texas Bluegrass TX 49-90 | 9.7 | 9.7 | 8.2 | 8.0 |
| Kelly | 6.3 | 6.1 | 4.4 | 4.3 |
| LSD (P = .05) | 1.679 | 1.738 | 1.875 | 1.621 |

TABLE 19-continued

Comparison of morphological traits of plant inflorescence - spikelets, florets, glumes - from panicles havested from a field nursery and plant height in 2005 at The Scotts Company facility at Gervais, Oregon.

| Variety | Florets/ Spikelet 1stWhorl (Count) | Florets/ Spikelet 3rdWhorl (Count) | Lower Glume Length 1stWhorl (mm) | Lower Glume Length 3rdWhorl (mm) |
|---|---|---|---|---|
| 'HB 329' | 4.6 | 5.0 | 3.7 | 3.6 |
| HB 129 | 8.6 | 7.0 | 3.1 | 3.2 |
| Reveille | 4.0 | 4.9 | 2.9 | 3.3 |
| Geronimo | 5.2 | 6.0 | 2.7 | 3.0 |
| Ascot | 3.8 | 4.3 | 2.9 | 2.9 |
| Midnight | 4.3 | 5.8 | 2.7 | 2.6 |
| Buckingham | 6.7 | 7.1 | 3.1 | 3.0 |
| Texas Bluegrass TX 51-90 | 8.8 | 8.5 | 3.6 | 3.3 |
| Texas Bluegrass TX 39-88 | 8.0 | 7.9 | 3.6 | 3.6 |
| Texas Bluegrass TX 49-90 | 8.7 | 8.6 | 5.4 | 5.0 |
| Kelly | 4.3 | 4.9 | 2.8 | 2.9 |
| LSD (P = .05) | 1.69 | 1.81 | 0.853 | 0.682 |

| Variety | Upper Glume Length 1stWhorl (mm) | Upper Glume Length 3rdWhorl (mm) | Plant Height (cm) |
|---|---|---|---|
| 'HB 329' | 3.6 | 3.7 | 35.8 |
| HB 129 | 3.5 | 3.3 | 58.3 |
| Reveille | 3.3 | 3.5 | 51.6 |
| Geronimo | 2.9 | 3.1 | 56.9 |
| Ascot | 3.1 | 3.1 | 38.2 |
| Midnight | 3.1 | 3.2 | 29.7 |
| Buckingham | 3.4 | 3.4 | 48.2 |
| Texas Bluegrass TX 51-90 | 4.2 | 4.2 | 48.1 |
| Texas Bluegrass TX 39-88 | 4.0 | 4.2 | 60.4 |
| Texas Bluegrass TX 49-90 | 6.0 | 5.4 | 56.2 |
| Kelly | 3.0 | 3.0 | 38.0 |
| LSD (P = .05) | 0.951 | 0.803 | 8.807 |

What is claimed is:

1. A new and distinct hybrid variety of (Texas bluegrass×Kentucky bluegrass)×Kentucky bluegrass plant, as herein illustrated and described and characterized by a moderately rapid establishment; a dark green, moderately dense turf; a wide leaf blade; moderately aggressive rhizome growth; a moderate level of cotton on the seed; and a low to medium-low seed yield potential.

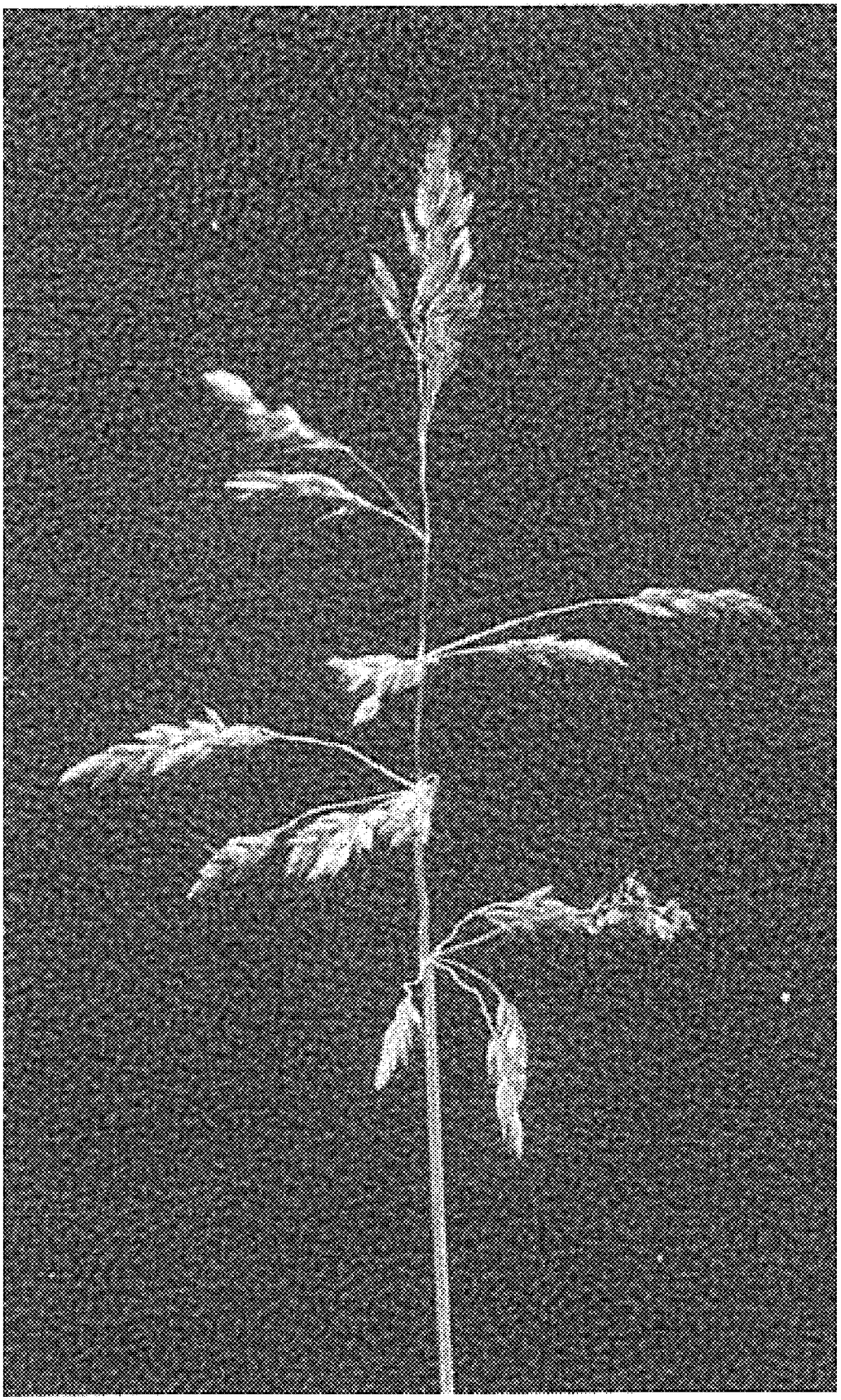

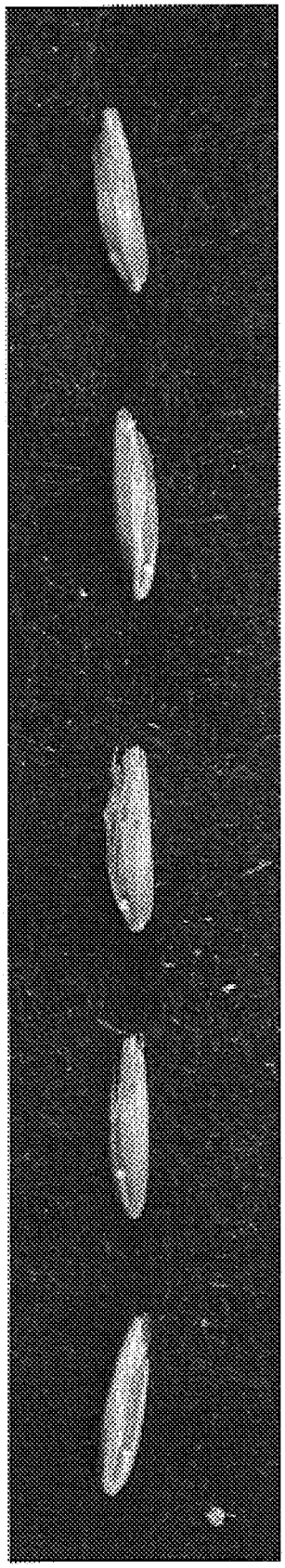

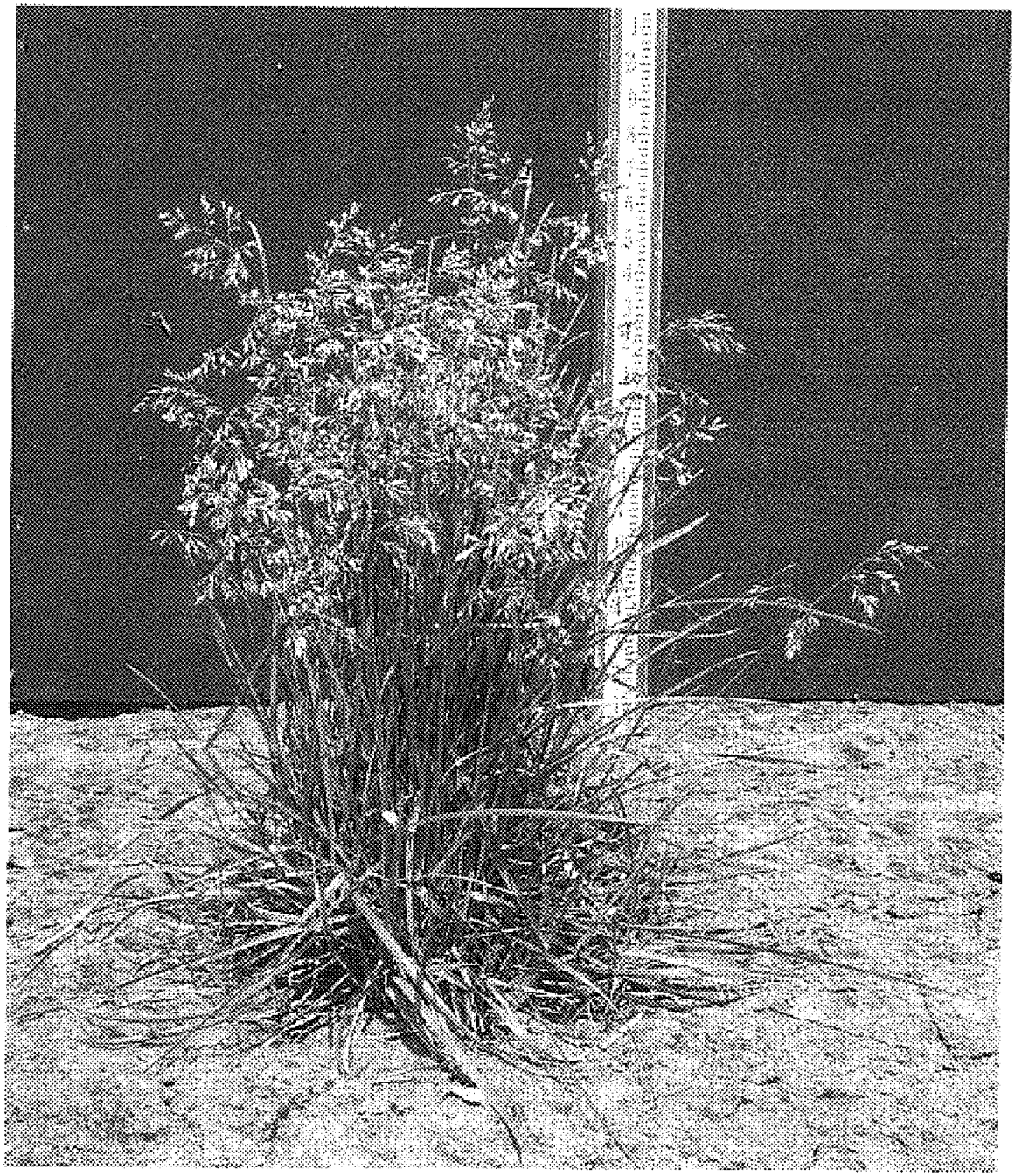

* * * * *